United States Patent [19]
Shaffer et al.

[11] Patent Number: 6,159,952
[45] Date of Patent: *Dec. 12, 2000

[54] METHOD OF TREATING BRONCHITIS WITH URIDINE TRIPHOSPHATE AND RELATED COMPOUNDS

[75] Inventors: Christy L. Shaffer; Richard C. Boucher, both of Chapel Hill; Janet L. Rideout, Raleigh; Karla M. Jacobus, Cary, all of N.C.

[73] Assignee: Inspire Pharmaceuticals, Inc., Durham, N.C.

[*] Notice: This patent issued on a continued prosecution application filed under 37 CFR 1.53(d), and is subject to the twenty year patent term provisions of 35 U.S.C. 154(a)(2).

[21] Appl. No.: 08/744,367

[22] Filed: Nov. 7, 1996

[51] Int. Cl.$^7$ .................................................... A61K 31/70
[52] U.S. Cl. .................................. 514/47; 514/50; 514/51
[58] Field of Search ................................ 514/45, 47, 46, 514/50, 51

[56] References Cited

U.S. PATENT DOCUMENTS

| | | | |
|---|---|---|---|
| 3,846,402 | 11/1974 | Eckstein et al. | 260/211.5 |
| 3,960,840 | 6/1976 | Secrist et al. | 260/211.5 |
| 4,501,729 | 2/1985 | Boucher et al. | . |
| 5,292,498 | 3/1994 | Boucher | 424/45 |
| 5,420,116 | 5/1995 | Puchelle et al. | 514/47 |
| 5,628,984 | 5/1997 | Boucher et al. | . |

FOREIGN PATENT DOCUMENTS

| | | |
|---|---|---|
| 2677250 | 5/1991 | France . |
| 2684299 | 2/1992 | France . |
| 9211016 | 9/1992 | WIPO . |
| WO 92/17488 | 10/1992 | WIPO . |
| WO 94 08593 | 4/1994 | WIPO . |
| WO 96 40059 | 12/1996 | WIPO . |

OTHER PUBLICATIONS

K. Svartengren et al., *Exp. Lung Res.* 22, 555–76 (1996).
S. Mason et al., *Br. J. Pharmacol.* 103,1649–56 (1991.
D. Drutz et al., *Drug Deve. Res.,* 37(3), 185 (1996).
S. Rooney et al., *Progr. Respir. Res.* 27, 84–91 (1994 (Under Separate Cover).
L. Gobran et al., *Am. J. Physiol.* 267, L625–33 (1994).
K. Olivier et al., *Am. J. Respir. Care Med.* 154, 217–23 (1996).
P. Noone et al., *Amer. J. Respir. And Crit. Care Med.* 153(4),A530(1996).
E. Rapaport et al. *Proc. Natl. Acad. Sci. USA* 78, 838–42 (1981.
K. Ng and L. Orgel, *Nucleic Acids Res.* 15(8), 3573–80 (1977.
Bassin, A. T. et al., "Prevention of ventilator–associated pneumonia", *Clin Chest med.* 16:No 1:195–208 (1995).
Kim, W.D., "Lung mucous: a clinician's view", *Eur. Respir. J.* 10:1914–1917 (1997).
Wanner, Adam MD, "The role of Mucous in Chronic Obstructive Pulmonary Disease", *Chest* 97:11S–15S (1990).
Wood, R. E. et al., "Recent advances in aerosol therapy", *J. Aerosol Med* 7:No 1:1–11 (1994).
Rooney, et al., "Signal Transduction Mechanisms Mediating Surfactant Phospholipid Secretion in Isolated Type II Cells," *Progr. Respir. Res.* 27;84–91 (1994.

*Primary Examiner*—Raymond Henley, III
*Attorney, Agent, or Firm*—Albert P. Halluin; John A. Bendrick; Howrey & Simon

[57] ABSTRACT

A method of promoting clearance of retained mucous secretions in the bronchi, bronchioles and small terminal airways of a subject in need of such treatment is disclosed. The method comprises administering to the bronchi of the subject a uridine phosphate such as uridine 5'-triphosphate (UTP), or $P^1,P^4$-di(uridine-5') tetraphosphate ($U_2P_4$), an analog of UTP, or any other analog, in an amount effective to promote mucociliary clearance and/or cough clearance of retained fluid in the bronchi, bronchioles and small terminal airways. Pharmaceutical formulations and methods of making the same are also disclosed. Methods of administering the same would include: aerosol inhalation, any liquid suspension (including nasal drops or spray), oral form (liquid or pill), injected, intra-operative instillation or suppository form.

13 Claims, No Drawings

METHOD OF TREATING BRONCHITIS WITH URIDINE TRIPHOSPHATE AND RELATED COMPOUNDS

INTRODUCTION

1. Technical Field

This invention relates to a method of removing retained mucous secretions from the bronchi, bronchioles and small terminal airways of a subject by administering uridine triphosphate and other purinergic receptor agonists.

2. Background of the Invention

Chronic bronchitis (CB) is excessive production of mucus in the bronchi accompanied by a recurrent cough that persists for at least three months of the year during at least two successive years. CB is the major non-asthmatic disease of the lung. This condition affects approximately 14 million Americans and is a major cause of death in the United States. Many different factors initiate CB, including cigarette smoking, environmental pollution, chronic infections and various genetic abnormalities. Of these factors, cigarette smoking is the most prevalent. Pathological changes in the lung consist of: (1) hypertrophy and hyperplasia of mucus-secreting glands in the bronchi, (2) increase in goblet cells, (3) disappearance or damage of cilia, and (4) chronic inflammatory changes and narrowing of small airways. Often, a bacterial or viral infection is present. Excess amounts of mucus are found in the airways and sometimes may occlude small bronchioles. Eventually, there may be scarring of the bronchial wall. Coughing is stimulated by retained mucus which cannot be adequately removed due to decreased cilia and lessened mucociliary clearance (K. Svartengen, et al., *Exp. Lung Res.* 22, 555–76 (1996)). It is important that bronchitis patients clear retained mucus through coughing, however, often coughing is ineffective in adequately removing these secretions because the bronchitis patient cannot inspire deeply enough to cause air to flow distal to retained secretions.

Current treatments for chronic bronchitis include antibiotic therapy, bronchodilators, anti-inflammatory agents and chest physiotherapy. These treatments are often palliative in nature rather than effective in treating and/or preventing the progression of this disease. While antibiotics are effective in treating exacerbations of bronchitis due to bacterial infections, the disadvantage of antibiotic therapy is that the patient may develop antibiotic resistance. There is increasing evidence that chronic bronchitis is caused by viral infections. The disadvantage of bronchodilators is that they sometimes have adverse cardiovascular side effects. As for anti-inflammatory agents, there is some controversy as to which stage in the progression of chronic bronchitis inflammation plays a role. None of these treatments have been successful in enhancing clearance of retained mucous secretions.

It is now known that nucleoside phosphates such as uridine 5'-triphosphate (UTP) and its analogs modulate components of the mucociliary clearance system. UTP has been shown to increase $Cl^-$ secretion, and hence water secretion, from airway epithelial cells in vitro (S. Mason, et al., *Br. J. Pharmacol.* 103, 1649–56 (1991); see also, U.S. Pat. No. 5,292,498 to R. Boucher (applicant intends the disclosure of this and all other patent references and publications cited herein be incorporated herein by reference). UTP has also been shown to increase cilia beat frequency in human airway epithelial cells in vitro (D. Drutz, et al., *Drug Dev. Res.* 37(3), 185 (1996)). UTP and other nucleotides have been shown to stimulate the release of surfactant phopholipids from type II alveolar cells (S. Rooney, et al., *Progr. Respir. Res.* 27, 84–91 (1994); L. Gobran, et al., *Am. J. Physiol.* 267, L625–33 (1994)). These effects have been shown to be mediated through a P2 receptor. The applicants believe that the release of surfactant or surface active molecules, caused as part of the treatment with UTP and related compounds, will improve compliance of the small airways and consequently improve gas exchange. Clinically, UTP has been shown to increase mucociliary lung clearance 2.5-fold in normal volunteers without any significant side-effects (K. Olivier, et al., *Am. J. Respir. Care Med.* 154, 217–23 (1996)). UTP has also been shown to significantly improve cough clearance in primary ciliary dyskinesia (PCD) patients relative to vehicle (saline) (P. Noone, et al., *Amer. J. Respir. And Crit. Care Med.* 153(4), A530 (1996)). Also, in a subset of these PCD patients, the rate of sputum expectoration appeared to be increased with inhalation of UTP versus saline (unpublished data of applicants). Additionally, a French biotechnology company, Laboratoires Synthelabo, has developed a pharmaceutical composition for treating nasal mucous fluid congestion under the trademark name rhinATP™ which uses adenosine triphosphate (ATP) as the active compound.

Because of UTP's demonstrated ability to increase hydration of mucous secretions, increase cilia beat frequency and improve mucociliary whole lung clearance of retained secretions, applicants were motivated to investigate whether UTP, its analogs and other purinergic receptor agonists could effectively treat acute and chronic bronchitis as defined herein.

SUMMARY OF THE INVENTION

A method of treating bronchitis in a subject in need of such treatment is disclosed. Bronchitis is defined to include chronic bronchitis, acute bronchitis and bronchiectasis. Cough clearance is defined as induction of lung mucus clearance by cough. The method of the present invention comprises administering by inhalation an aerosol suspension of respirable particles to the bronchi, bronchioles and terminal small airways of the subject, the particles selected from the group consisting of general Formula I, i.e., uridine triphosphate [UTP] and its analogs, general Formula II, i.e., $P^1P^4$—di(uridine-5') tetraphosphate [$U_2P_4$] and its analogs, general Formula III, i.e., adenosine 5'-triphosphate [ATP] and its analogs, or general Formula IV, i.e., cytidine 5'-triphosphate [CTP] and its analogs, with the particles of Formula I, II, III or IV administered in an amount effective to hydrate retained bronchial mucous secretions and increase cilia beat frequency in the bronchi, bronchioles and terminal small airways of the subject, whereby the retained mucous secretions are more easily transported from the bronchi, bronchioles and small terminal airways via mucociliary action.

UTP and its analogs are depicted in general Formula I:

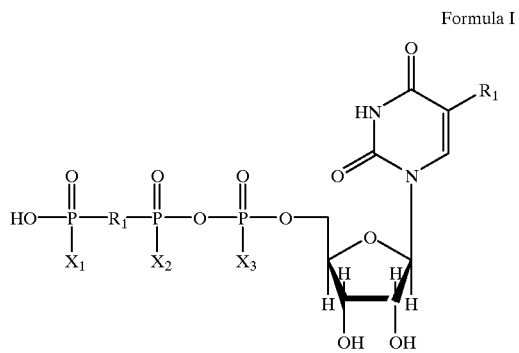

Formula I wherein:

$X_1$, $X_2$, and $X_3$ are each independently either $O^-$ or $S^-$. Preferably, $X_2$ and $X_3$ are $O^-$.

$R_1$ is O, imido, methylene, or dihalomethylene (e.g., dichloromethylene, diflouromethylene). Preferably, $R_1$ is oxygen or difluoromethylene.

$R_2$ is H or Br. Preferably, $R_2$ is H. Particularly preferred compounds of Formula I are uridine 5'-triphosphate (UTP) and uridine 5'-O-(3-thiotriphosphate) (UTPγS).

A dinucleotide is depicted by the general Formula II:

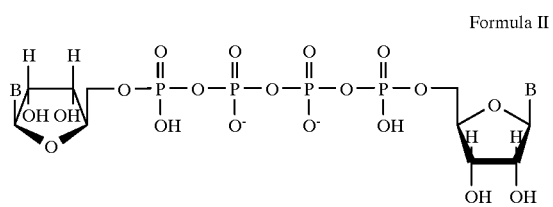

Formula II wherein:

B is uracil or adenine, attached as shown in Formulae I and III.

ATP and its analogs are depicted by general Formula III:

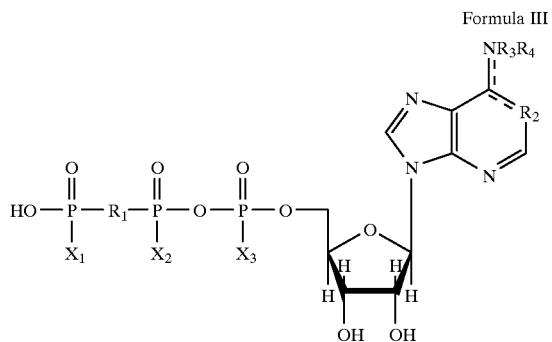

Formula III wherein:

$R_1$, $X_1$, $X_2$ and $X_3$ are defined as in Formula I.

$R_3$ and $R_4$ are H while $R_2$ is nothing and there is a double bond between N-1 and C-6 (adenine), or $R_3$ and $R_4$ are H while $R_2$ is O and there is a double bond between N-1 and C-6 (adenine 1-oxide), or $R_3$, $R_4$ and $R_2$ taken together are —CH=CH—, forming a ring from N-6 to N-1 with a double bond between N-6 and C-6 (1,N6-ethenoadenine).

CTP and its analogs are depicted by general Formula IV:

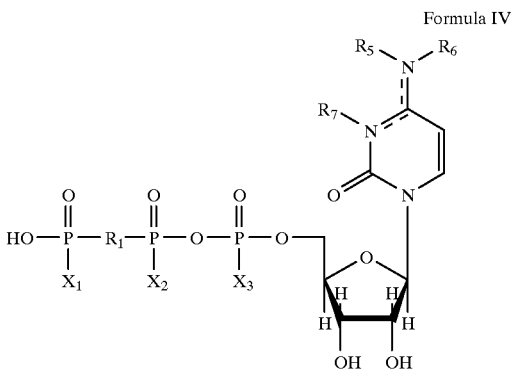

Formula IV wherein:

$R_1$, $X_1$, $X_2$ and $X_3$ are defined as in Formula I.

$R_5$ and $R_6$ are H while $R_7$ is nothing and there is a double bond between N-3 and C-4 (cytosine), or $R_5$, $R_6$ and $R_7$ taken together are —CH=CH—, forming a ring from N-3 to N-4 with a double bond between N-4 and C-4 (3,N4-ethenocytosine).

For simplicity, Formulae I–IV herein illustrate the active compounds in the naturally occuring D-configuration, but the present invention also encompasses compounds in the L-configuration, and mixtures of compounds in the D- and L-configurations, unless otherwise specified. The naturally occuring D-configuration is preferred.

A second aspect of the present invention is the use of UTP, or a compound of Formula II, III or IV, for the manufacture of a medicament for carrying out a therapeutic method of treatment as given above.

A third aspect of the present invention is a pharmaceutical composition comprising UTP, or a compound of Formula II, III or IV, in a pharmaceutical carrier in an amount effective to hydrate mucous secretions in the bronchi, bronchioles and small terminal airways; increase cilia beat frequency in the bronchi, bronchioles and small terminal airways; and enhance clearance of retained mucous secretions in the bronchi, bronchioles and small terminal airways.

DETAILED DESCRIPTION OF THE INVENTION

The method of the present invention may be used to remove mucous secretions retained in the mainstem bronchi and small airways of a subject for any reason, including (but not limited to) retention of secretions arising from airway diseases such as acute or chronic bronchitis, bronchiectasis, asthma and emphysema. The compound uridine triphosphate was identified as a potent agonist of the $P_{2Y2}$ purinergic receptor in human airway epithelial preparations. The novel feature of uridine triphosphate as compared to other treatments for bronchitis, such as antibiotics, bronchodilators and anti-inflammatory agents is that this compound promotes hydration, stimulation of mucociliary and/or cough to enhance the removal of retained bronchial secretions.

The present invention is concerned primarily with the treatment of human subjects, but may also be employed for the treatment of other mammalian subjects, such as dogs and cats, for veterinary purposes.

The term "uridine triphosphate" as used herein, include the pharmaceutically acceptable salts thereof, such as (but not limited to) an alkali metal salt such as sodium or potassium; an alkaline earth metal salt such as magnesium or calcium; or an ammonium or tetraalkyl ammonium salt, i.e., $NX_4+$ (wherein X is $C_{1-4}$ alkyl). Pharmaceutically acceptable salts are salts that retain the desired biological activity of the parent compound and do not impart undesired toxicological effects.

The active compounds disclosed herein may be administered to the lungs of a patient by any suitable means, but are preferably administered by administering an aerosol suspension of respirable particles comprised of the active compound, which the subject inhales. The respirable particles may liquid or solid. The quantity of the active compound included may be an amount sufficient to achieve dissolved concentrations of the active compound on the bronchial surfaces of the subject of from about $10^{-7}$ to about $10^{-1}$ Moles/liter, and more preferably from about $10^{-6}$ to about $5\times10^{-2}$ Moles/liter.

Depending upon the solubility of the particular formulation of active compound administered, the daily dose to promote secretion drainage may be divided among one or several unit dose administrations. The total daily dose for UTP may range from about 6 to 720 milligrams of respirable uridine triphosphate for a human subject, depending upon the age and condition of the subject. A currently preferred unit dose for UTP is about 2 to 100 milligrams of respirable uridine triphosphate particles given at a regimen of three to four administrations per day.

The liquid or solid particulate uridine triphosphate prepared for practicing the present invention should include particles of respirable size: that is, particles of a size sufficiently small to pass through the mouth and larynx upon inhalation and into the bronchi, bronchioles and terminal small airways of the lungs. In general, particles ranging from about 1 to 5 microns in size are considered respirable.

Some compounds of Formula I, III and IV can be made by methods which are well known to those skilled in the art; some are commercially available, for example, from Sigma Chemical Company, PO Box 14508, St. Louis, Mo. 63178. Compounds of Formula II can be made in accordance with known procedures, or variations thereof which will be described by: P. Zamecnik, et al., *Proc. Natl. Acad. Sci. USA* 89, 838–42 (1981); and K. Ng and L. E. Orgel, *Nucleic Acids Res.* 15(8), 3572–80 (1977).

In the manufacture of a formulation according to the invention, active agents or the physiologically acceptable salts thereof are typically admixed with, inter alia, an acceptable carrier. The carrier must be acceptable in that it is compatible with any other ingredients in the formulation and must not be deleterious to the patient. The carrier may be a solid or a liquid, or both. The formulations of the invention may incorporate one or more active compounds, and these formulations may be prepared by any of the well-known techniques of pharmacy consisting essentially of admixing the components.

Aerosols of liquid particles comprising the active compound may be produced by any suitable means, such as with a pressuredriven aerosol nebulizer or an ultrasonic nebulizer. See, e.g., U.S. Pat. No. 4,501,729. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or a dilute aqueous alcoholic solution, preferably made isotonic with body fluids by the addition of, for example, sodium chloride. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquefied propellant. During use these devices discharge a metered volume, typically from 10 to 150 µl, to produce a fine particle spray containing the active ingredient. Suitable propellants include non-chlorofluorocarbon propellants as well as certain chlorofluorocarbon compounds, for example, dichlorodifluoromethane, trichlorofluoromethane, dichlorotetrafluoroethane and mixtures thereof. The formulation may additionally contain one or more cosolvents, for example, ethanol, surfactants, such as oleic acid or sorbitan trioleate, antioxidants and suitable flavoring agents.

Compositions containing respirable dry particles of micronized uridine triphosphate may be prepared by grinding the dry uridine triphosphate with a mortar and pestle, and then passing the micronized composition through a 400 mesh screen to break up or separate out large agglomerates. In dry powder delivery, the UTP may be formulated alone or in combination with diluent or carrier, such as sugars where the compounds may be intimately incorporated in the matrix through glassification or simply admixed with the carrier (i.e., lactose, sucrose, trehalose, mannitol) or other acceptable excipients for lung or airway delivery. The dry powder may be obtained by methods known in the art, such as spray-drying, milling, freeze-drying, etc.

The aerosol, whether formed from solid or liquid particles, may be produced by the aerosol generator at a rate of from about 10 to 150 liters per minute, more preferable from about 30 to 150 liters per minute, and most preferable about 60 liters per minute. Aerosols containing greater amounts of medicament may be administered more rapidly.

The particulate uridine triphosphate composition may optionally contain a dispersant which serves to facilitate the formation of an aerosol. A suitable dispersant is lactose, which may be blended with the uridine triphosphate in any suitable ratio (e.g., a 1 to 1 ratio by weight).

Another means of administering the active compound to the bronchi of the subject would involve administering a liquid/liquid suspension (either a nasal spray of respirable particles which the subject inhales, or nasal drops of a liquid formulation, or eye drops of a liquid formulation) comprised of the active compound. Liquid pharmaceutical compositions of the active compound for producing a nasal spray or nasal or eye drops may be prepared by combining the active compound with a suitable vehicle, such as sterile pyrogen free water or sterile saline by techniques known to those skilled in the art.

Another means of administering the active compound would involve oral administration, in which pharmaceutical compositions containing compounds of Formula I, II, III or IV are in the form of tablets, lozenges, aqueous or oily suspensions, dispersible powders or granules, emulsion, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Another mean of administering the active compound to the bronchi of the subject would involve a suppository form of the active compound, such that a therapeutically effective amount of the compound reaches the lung via systemic absorption and circulation.

Another means of administering the active compound would involve direct intra-operative instillation of a gel, cream, or liquid suspension form of a therapeutically effective amount of the active compound. Such intra-operative instillation could take place during bronchoscopy, thoracotomy or during surgery to remove non-functioning, hyperinflated sections of the lung, as is sometimes required in advanced stages of bronchitis, bronchiectasis or emphysema.

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be apparent to those skilled in the art of organic synthesis as well as the conditions necessary to attach and remove such groups.

The invention is illustrated further by the following example which is not to be construed as limiting the invention in scope or spirit to the specific procedures described in it.

EXAMPLE 1

Treatment of Chronic Bronchitis

Uridine 5'-triphosphate (UTP) is administered to patients diagnosed with chronic bronchitis (based upon the American Thoracic Society definition: excess mucus production, occurring on most days for at least three months of the year for at least two successive years). The efficacy of UTP is determined by measuring the clearance of an inhaled radio-labeled particle from the lung by radio-nucleotide scanning techniques. Each subject inhales an aerosol of iron oxide labeled with Technetium 99m ($^{99}Tc$—$Fe_2O_3$). Subjects inhale the aerosol for approximately 5 minutes. Subjects are then seated in front of a gamma camera, and for the next 10 minutes subjects randomly inhale either a saline control, or 0.5–45 mg/ml UTP. After this inhalation, subjects remain seated in front of the gamma camera for the next two hours to measure clearance of the radiolabeled iron oxide. Some studies include subjects that perform controlled coughs in this time period, and sputum is collected, weighed and volume recorded throughout the study and stored for additional analysis of sputum rheology or ion content. Subjects repeat this procedure on subsequent days as appropriate to the number of doses under study.

The efficacy of aerosolized UTP in treating chronic bronchitis is demonstrated by an improvement in mucociliary and/or cough clearance of Technectium 99m as compared to the saline vehicle alone.

Approximately 24 hours following each inhalation exposure, subjects return for a 30-minute scan of residual radioactivity in the lung. During this time they sit continuously in front of the gamma camera.

Safety data is collected by monitoring heart rate, ECG, blood pressure, oxyhemoglobin saturation by pulse oximetry prior to, during, and after inhalation for all dosing periods. All patients during all phases of the study are monitored for any adverse reactions during each dosing period, beginning with inhalation of study drug and ending after the 30-minute scan at 24 hours.

What is claimed is:

1. A method of increasing mucociliary clearance and/or cough clearance in a subject in need of such treatment, said method comprising:

administering to the subject a compound of Formula II or IV; or a pharmaceutically acceptable salt thereof, in a pharmaceutical carrier having an amount of said compound effective to mucociliary clearance and/or cough clearance:

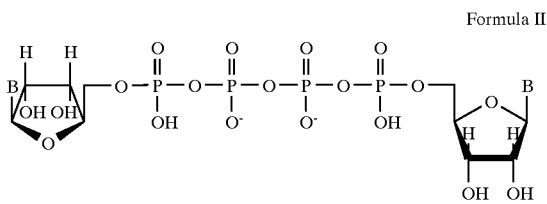

Formula II wherein:
B is uracil or adenine attached as in Formula III;
wherein:

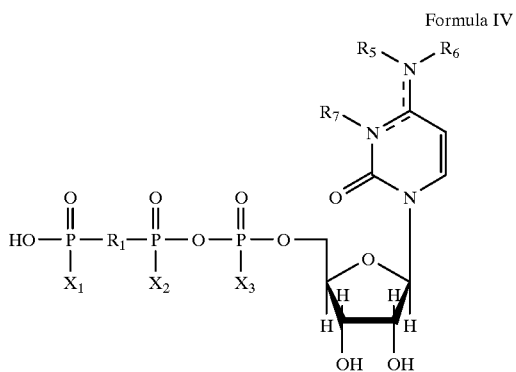

Formula IV wherein:
- $R_1$ is selected from the group consisting of O, imido, methylene and dihalomethylene, $X_1$, $X_2$ and $X_3$ are each independently selected from the group consisting of OH and SH,
- $R_5$ and $R_6$ are H while $R_7$ is nothing and there is a double bond between N-3 and C-4 (cytosine), or
- $R_5$, $R_6$ and $R_7$ taken together are —CH=CH—, forming a ring from N-3 to N-4 with a double bond between N-4 and C-4 (3,N4-ethenocytosine).

2. A method according to claim 1, wherein said compound is delivered by administering a nebulized aerosol suspension or solution of said compound to the nasopharyngeal airways of said subject, such that a therapeutically effective amount of said compound contacts the bronchi, bronchioles and small terminal airways of said subject either directly or by systemic absorption and circulation.

3. A method according to claim 1, wherein said compound is delivered by administering an oral form of said compound, such that a therapeutically effective amount of said compound contacts the bronchi, bronchioles and small terminal airways of said subject via systemic absorption and circulation.

4. A method according to claim 1, wherein said compound is delivered by administering a liquid/liquid suspension, powder or spray, of said compound to the nasopharyngeal airways of said subject, such that a therapeutically effective amount of said compound contacts the bronchi, bronchioles and small terminal airways of said subject either directly or via systemic absorption and circulation.

5. A method according to claim 1, wherein said compound is delivered by administering an injected form of said compound, such that a therapeutically effective amount of said compound contacts the bronchi, bronchioles and small terminal airways of said subject via systemic absorption and circulation.

6. A method according to claim 1, wherein said compound is delivered by administering a suppository form of said compund, such that a therapeutically effective amount of said compound contacts the bronchi, bronchioles and small terminal airways of said subject via systemic absorption and circulation.

7. A method according to claim 1, wherein said compound is delivered by administering an intra-operative instillation of a gel, cream, powder, foam, crystals or liquid suspension form of the active compound such that a therapeutically effective amount of said compound contacts the bronchi, bronchioles and small terminal airways of said subject via systemic absorption and circulation.

8. A method according to claim 1, wherein said compound is administered in an amount sufficient to achieve concentrations thereof on the surfaces of the bronchi, bronchioles and small terminal airways of said subject of from about $10^{-7}$ to about $10^{-1}$ moles/liter.

9. A method according to claim 1, wherein $X_2$ and $X_3$ are OH.

10. A method according to claim 1, wherein $R_1$ is oxygen.

11. A method according to claim 1, wherein $R_2$ is H.

12. A method according to claim 1, wherein said compound of Formula II is selected from the group consisting of $P_1$,$P_4$-di(uridine-5')tetraphosphate ($U_2P_4$) and $P_1$,$P_4$-di (adenosine-5')tetraphosphate ($A_2P_4$) and pharmaceutically acceptable salts thereof.

13. A method according to claim 1, wherein said compound of Formula IV is selected from the group consisting of cytidine 5'-triphosphate (CTP), 3,$N^4$-ethenocytidine 5'-triphosphate and the pharmaceutically acceptable salts thereof.

* * * * *

UNITED STATES PATENT AND TRADEMARK OFFICE
CERTIFICATE OF CORRECTION

PATENT NO. : 6,159,952
DATED : December 12, 2000
INVENTOR(S) : Shaffer et al.

It is certified that error appears in the above-identified patent and that said Letters Patent is hereby corrected as shown below:

<u>Title page,</u>
Item [56], References Cited, U.S. PATENT DOCUMENTS, insert
-- 5,635,160 6/1997 Stutts, et al. --

<u>Column 3,</u>
Lines 3-15, delete

" FORMULA I

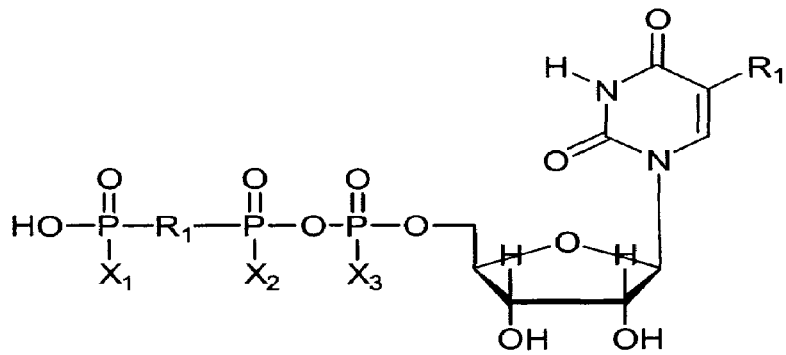

and insert
--

FORMULA I

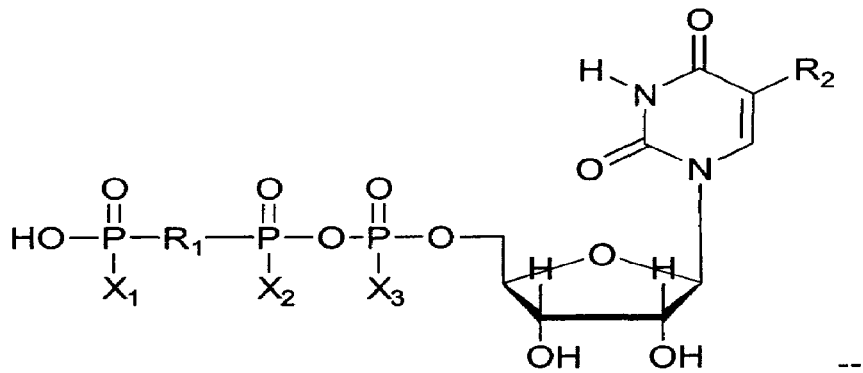

--

UNITED STATES PATENT AND TRADEMARK OFFICE
CERTIFICATE OF CORRECTION

PATENT NO. : 6,159,952
DATED : December 12, 2000
INVENTOR(S) : Shaffer et al.

It is certified that error appears in the above-identified patent and that said Letters Patent is hereby corrected as shown below:

Column 3,
Lines 43-56,

FORMULA III

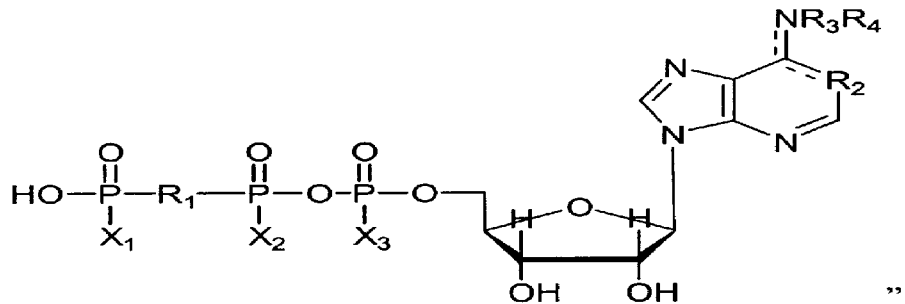

"

and insert

-- FORMULA III

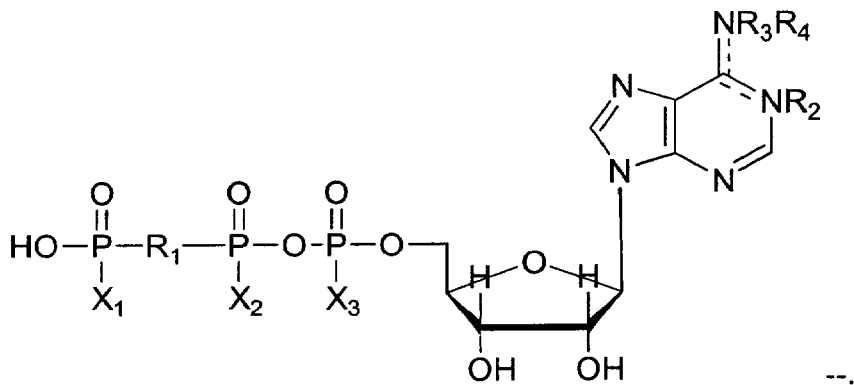

--.

UNITED STATES PATENT AND TRADEMARK OFFICE
CERTIFICATE OF CORRECTION

PATENT NO.    : 6,159,952
DATED         : December 12, 2000
INVENTOR(S)   : Shaffer et al.

It is certified that error appears in the above-identified patent and that said Letters Patent is hereby corrected as shown below:

<u>Column 9,</u>
Line 12, change "Formula III" to -- Formulae I and III --.

Signed and Sealed this

Thirtieth Day of July, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,159,952  
DATED : December 12, 2000  
INVENTOR(S) : Shaffer et al.

It is certified that error appears in the above-identified patent and that said Letters Patent is hereby corrected as shown below:

<u>Title page,</u>
Item [73], Assignee, should read:
-- Inspire Pharmaceuticals, Inc., Durham, N.C.; and University of North Carolina, Chapel Hill, N.C. --

Signed and Sealed this

Twenty-seventh Day of January, 2004

JON W. DUDAS
*Acting Director of the United States Patent and Trademark Office*